(12) United States Patent
Noble

(10) Patent No.: US 11,491,029 B2
(45) Date of Patent: Nov. 8, 2022

(54) SIZER, INTRODUCER AND TEMPLATE DEVICE

(71) Applicant: Poriferous, LLC, Newnan, GA (US)

(72) Inventor: Aaron Matthew Noble, Newnan, GA (US)

(73) Assignee: Poriferous, LLC, Newnan, GA (US)

( * ) Notice: Subject to any disclaimer, the term of this patent is extended or adjusted under 35 U.S.C. 154(b) by 255 days.

(21) Appl. No.: 16/744,905

(22) Filed: Jan. 16, 2020

(65) Prior Publication Data
US 2020/0222207 A1    Jul. 16, 2020

Related U.S. Application Data

(60) Provisional application No. 62/793,225, filed on Jan. 16, 2019.

(51) Int. Cl.
*A61F 2/46* (2006.01)
*A61B 17/88* (2006.01)
*A61F 2/28* (2006.01)

(52) U.S. Cl.
CPC ........ *A61F 2/4657* (2013.01); *A61B 17/8863* (2013.01); *A61F 2002/2878* (2013.01); *A61F 2002/4658* (2013.01)

(58) Field of Classification Search
CPC ............ A61F 2/4657; A61F 2002/2878; A61F 2002/4658; A61F 2002/4659; A61F 2/4603; A61B 17/8863
See application file for complete search history.

(56) References Cited

U.S. PATENT DOCUMENTS 6,440,065 B1    8/2002  Hered
9,913,704 B1 *  3/2018  Yaremchuk ............... A61F 2/02

FOREIGN PATENT DOCUMENTS

EP    2201899       6/2010
EP    2201899 A1 *  6/2010   ......... A61B 17/0231

OTHER PUBLICATIONS

Depuy Synthes, "Comprehensive solutions for orbital floor repair and reconstruction", 2018, jnjmedicaldevices.com (Year: 2018).*
PCT Patent Application No. PCT/US2020/013901, International Search Report and Written Opinion, dated Apr. 7, 2020, 6 pages.

* cited by examiner

*Primary Examiner* — Bruce E Snow
(74) *Attorney, Agent, or Firm* — Kilpatrick Townsend & Stockton LLP

(57) ABSTRACT

Embodiments of the present disclosure relate generally to a Sizer, Introducer, and Cutting Template Device. Embodiments find particular use as a sizer, introducer, and cutting template device for an orbital floor implant surgery. The disclosed device allows a surgeon or other practitioner to use a single component for sizing, introducing, and cutting a template for an orbital floor implant.

7 Claims, 2 Drawing Sheets

SIZER, INTRODUCER AND TEMPLATE DEVICE

This application claims the benefit of U.S. Provisional Application Ser. No. 62/793,225, filed Jan. 16, 2019 titled "Sizer, Introducer and Template Device," the entire contents of which are hereby incorporated by reference.

FIELD OF THE DISCLOSURE

Embodiments of the present disclosure relate generally to a Sizer, Introducer, and Cutting Template Device. Embodiments find particular use as a sizer, introducer, and cutting template device for an orbital floor implant surgery. The disclosed device allows a surgeon or other practitioner to use a single component for sizing, introducing, and cutting a template for an orbital floor implant.

BACKGROUND

During implant surgery, a surgeon or other practitioner will initially determine the appropriate size of the implant to be used. In some instances, an actual implant is used for sizing. For example, during repair of the orbital floor, an orbital implant may be used for sizing. However, this can be wasteful because if a particular implant used for sizing is not ultimately used (e.g., an incorrect size was initially selected), that implant is wasted. If this sizing process happens more than once, multiple implants are wasted, resulting in added expense and added surgery time. Additionally, once the appropriate implant size is selected, it may still need to be trimmed for an exact fit. Improvements to this surgical process are desirable.

BRIEF SUMMARY

Embodiments of the present disclosure thus provide a single component that functions as a sizer, introducer, and cutting template. Disclosed embodiments find particular use as a sizer, introducer, and cutting template device for an orbital floor implant surgery.

Certain embodiments provide a device, comprising: a body comprising first and second ends, each of the first and second ends having a contour that corresponds anatomically to the orbital floor, each of the first and second ends having differing sizes and being associated with a size indicator, the device comprising a nonporous material. The nonporous material may be high density polyethylene. The material may be a polymer material. The device may be made of a material that can be cut and shaped.

Embodiments also provide a method for identifying an appropriately sized implant, shaping the implant, and introducing the implant, comprising using the above-described device. The steps may include identifying an appropriately sized implant comprises positioning the device with respect to the patient's orbital floor and using the size indicators and item catalog number in order to identify an appropriately shaped implant. Shaping the implant may comprise trimming the device and using the trimmed device to shape the implant. Introducing the implant may comprise positioning the implant under the device and positioning the implant with respect to the orbital floor.

DETAILED DESCRIPTION

Figure 1:
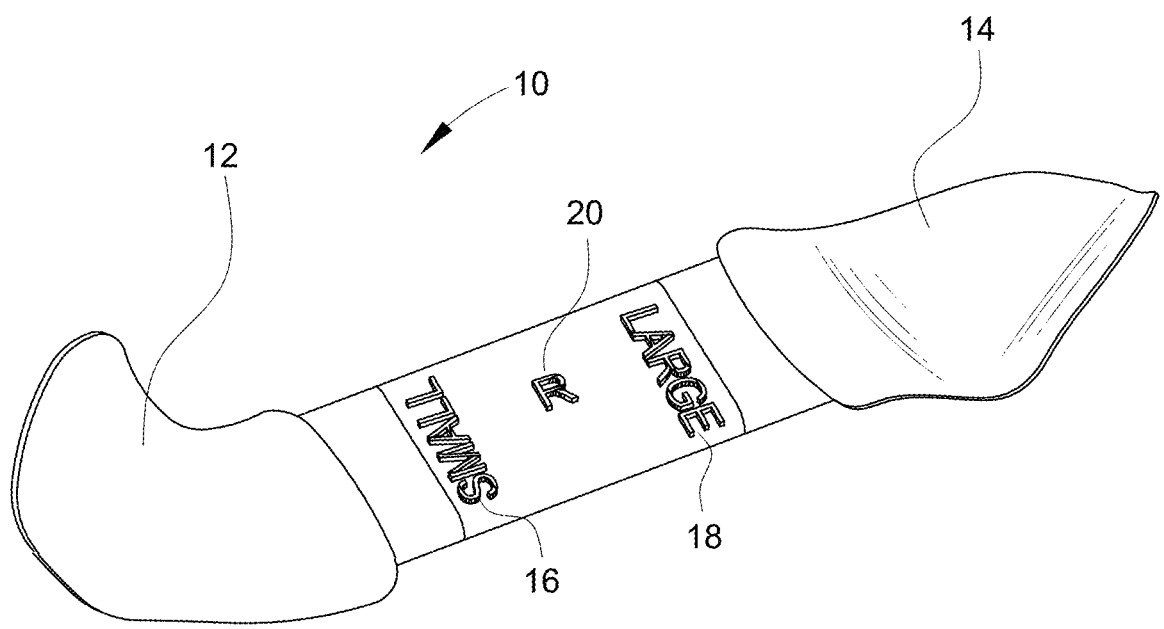
FIG. 1 shows a top perspective view of one embodiment of a sizer, introducer, and cutting template device.
Figure 2:
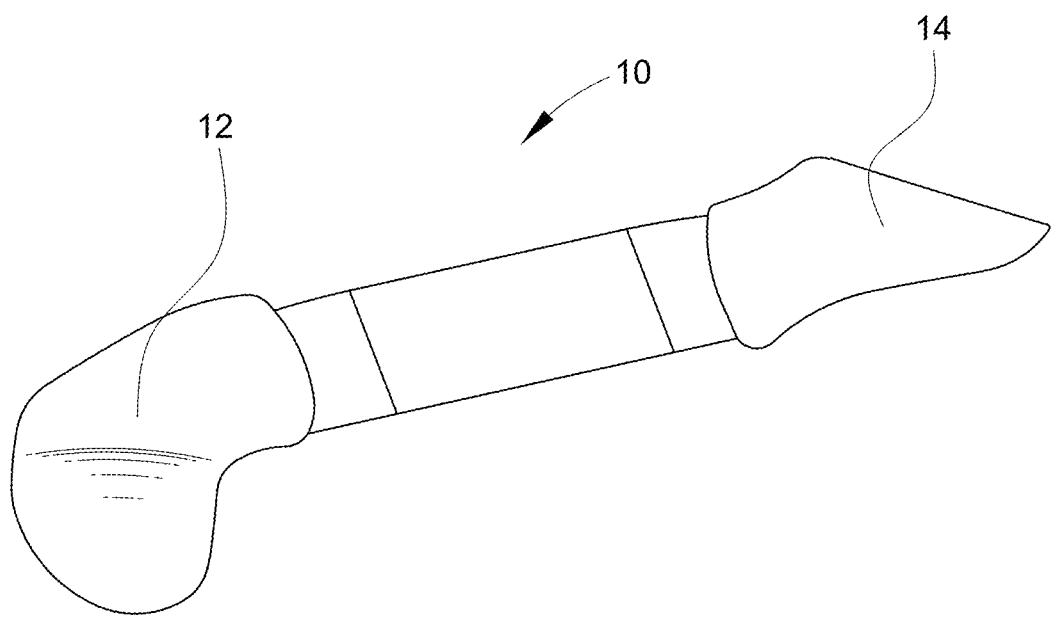
FIG. 2 shows a bottom perspective view of the device of FIG. 1.

Embodiments of the present disclosure provide a single component device 10 that may be used as a sizer, introducer, and cutting template device. As shown by FIGS. 1 and 2, the device 10 has two ends 12, 14 that are shaped similarly to the orbital floor at a location at which an implant would be positioned. A first end 12 may be labeled with a first size indicator 16, and the second end 14 may be labeled with a second size indicator 18. In this example, the first size indicator 16 is "small" and the second size indicator 18 is "large." It should be understood, however, that alternate and additional size indicators may be used. For example, a specific implant size or number may be used as the indicator(s). Additionally, although the device is shown as having two ends 12, 14, it is possible for the device to be "t" shaped or star-shaped, so that more than two ends are provided. For example, there may be three, four, five or more ends, with each end having its own size indicator or indicia. Regardless of the number of ends provided on the device, each of the ends should be sized to correspond to an actual implant size. The ends 12, 14 will generally have different sizes, contours, or other features that correspond to implants of differing sizes, contours, or other features.

Figure 3:
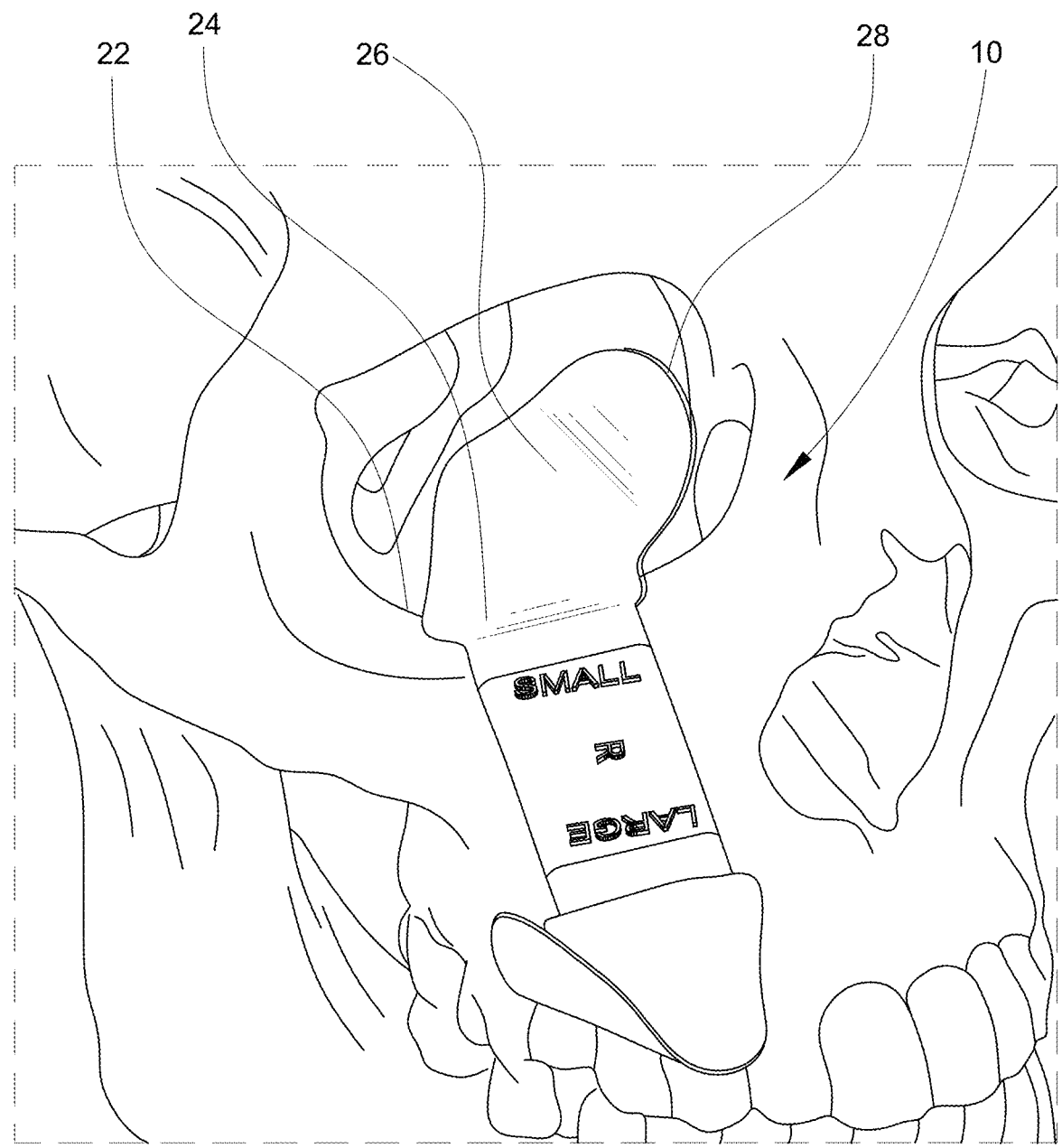
FIG. 3 shows the device of FIG. 1 in use during an orbital floor implant surgery.

The device 10 may also be sided, meaning that there may be provided a right side version and a left side version. The "side" may be marked directly on the device body 20, for example, by an "R" or "L" as shown. As shown by FIGS. 1 and 3, the body 20 may function like a handle and provides a connecting feature for the at least two ends 12, 14.

As shown by FIG. 3, the ends 12, 14 have contours or curvatures that generally correspond to or otherwise contour with the orbital floor 22. In a specific example, each end 12, 14 may be provided with a ridge 24 that extends/curves into a concave surface 26. An outer edge 28 of the concave surface may have a stronger upward curve, with a radius of curvature of about 75-90°. The ridge 24 may be shaped similar to a speed bump. It is intended to be positioned over the patient's orbital bone, such as the zygomatic arch. In use, the ridge 24 can rest over or against the bone, allowing the concave surface 26 to fill the remainder of the eye socket space. This positioning allows the surgeon or other practitioner to identify the most optimal implant size to be used. In addition to being used as an implant sizer, the device 10 may also be used for assisting with the introduction of the implant, as well as sizing and shaping of the final implant to be used.

For example, at the time of the surgery, the device 10 may be used in conjunction with a retractor to progressively lift and identify the defect margins. In one method, one or both of the ends 12, 14 of the device 10 may be used to help lift tissue. The ends 12, 14 may then be used as an implant sizer in order to determine the correct implant size (e.g., large or small) based on size indicators 16, 18 at the ends 12, 14 of the device. This allows the device 10 to be used for sizing prior to opening of an actual sterile implant, which can be more efficient in managing operating room surgical time and costs. (It is believed that prior to the development of the disclosed device, surgeons would use actual implants for this sizing step, which presents the possibility of opening more than one implant package during a surgery that would otherwise require only a single implant.)

Once the ideal implant size is selected, the device can be repeatedly removed and replaced against the orbital bone and used for sizing. For example, the device 10 may be of a material and thickness that allows it to be trimmed using scissors, or other cutting instruments, until the template (the concave surface 26 at the end) has been shaped into the ideal implant shape, size, and profile. The surface tension of the device allows it to be marked with a surgical marker for establishing of the orbital rim margin if the final implant is to be trimmed to fit deeply into the orbit.

Following the shaping of the device, the correctly determined size of implant is pulled from inventory and opened. If the implant should be shaped prior to implantation, the outline of the trimmed device 10 may be used in order to shape the implant. The stock implant is underlaid with respect to the device 10 (meaning that the implant is positioned under the device 10) and secured in orientation using clamping hemostats or any other appropriate clamping devices. Using the trimmed device 10 as an introducer guide in this way provides certain benefits. For example, the device 10 allows sliding of the implant into position without loading tissues of the orbit. The device can have a smooth surface in order to prevent "catus-ing" of the tissue (which occurs when tissue adheres to the implant or any other feature being used as an introducer). The smooth surface may be provided on one or both surfaces of the device end. The smooth surface may be polished, coated, or treated in any other appropriate way to prevent tissue adhesion.

Use of the device this way also allows the implant to be cut into shape using scissors or other appropriate cutting instrument. In other words, the modified device can be used as an implant sizer. The modified device and implant are placed back into the orbit using a retractor to assist in lifting tissues until the implant with the underlaid device 10 is in place. The clamps are removed and the device 10 is removed, leaving the implant in position. Fixation, if required, is carried out and the used device 10 may be discarded.

It is possible for the disclosed device 10 to be provided as a separate catalog item—as a sterile, disposable device. The device may be provided in sterile packaging. It is also possible for the device to be pre-packaged with one or more implant sizes.

In one specific embodiment, the implant template ends are about 0.4 mm thick. It is possible for the thickness to range from about 0.2 mm to about 0.8 mm. The device 10 may be made of the same high-density polyethylene as Su-Por implants (which are designed and manufactured by Poriferous LLC in Newnan, Ga.) but in a solid, non-porous form. The solid, nonporous nature of the device allows ease of its use as an introducer, preventing tissue adherence that may occur with use of a porous material. In one specific example, the material is high density polyethylene (HDPE). In another example, the material is a polymer. In further example, the material is any appropriate material that can be cut and shaped. The material should generally be a biocompatible biomaterial for contact with human tissue.

The material may be molded into a right or left sided, pre-shaped, non-porous orbital floor sizer, introducer, and cutting template, containing a larger pattern on one end and a smaller pattern on the other. (The device is not intended to be implanted, but rather to assist in the implantation of an orbital floor implant.)

The device may then be packaged in double peel Tyvek pouches, packaged with a product information sheet, and boxed. The box can be sealed on one end with a tamper evident seal, while the other end is sealed with a product label that contains product information. This configuration of materials is designed to prevent damage to the sterile barrier system and its contents from the time of production and assembly until the point of use. The packaged device may be EO sterilized, providing a sterile, single-use, non-implantable class I device.

In use, a practitioner selects the device catalog number required according to the side of the patient's defect from the company's listing of products. Once the device is ordered and shipped and surgery is scheduled, the use of the device is as outlined above. The device may be marked with the corresponding implant order number for proper selection from inventory.

The subject matter of certain embodiments of this disclosure is described with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

It should be understood that different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Changes and modifications, additions and deletions may be made to the structures and methods recited above and shown in the drawings without departing from the scope or spirit of the invention disclosure and the following claims.

What is claimed is:

1. A device, comprising:
a body comprising first and second ends, each of the first and second ends having a contour that corresponds to an orbital floor implant, each of the first and second ends having differing sizes and being associated with an implant indicia,
the first and second ends comprising trimmable ends comprising a polymer nonporous material with a thickness in the range of about 0.2 mm to about 0.8 mm.

2. The device of claim 1, wherein the nonporous material comprises high density polyethylene.

3. The device of claim 1, wherein the polymer nonporous material is biocompatible and can be cut and shaped.

4. A method using the device of claim 1, the method comprising using the device to identify an appropriately sized orbital floor implant, using the device to simulate the installation of the orbital floor implant, after using the device to simulate the installation of the orbital floor implant using the device to shape the orbital floor implant, and using the device to introduce the orbital floor implant to an orbital floor to be repaired.

5. The method of claim 4, wherein identifying an appropriately sized implant comprises positioning the device with respect to the patient's orbital floor and using the implant indicia on the device and an item catalog number in order to identify a corresponding orbital floor implant.

6. The method of claim 4, wherein shaping the implant comprises trimming the device and using the trimmed device to shape the orbital floor implant.

7. The method of claim 4, wherein introducing the orbital floor implant comprises positioning the orbital floor implant under the device and positioning the orbital floor implant with respect to the orbital floor.

\* \* \* \* \*